United States Patent [19]

Abidin et al.

[11] Patent Number: 5,275,606
[45] Date of Patent: Jan. 4, 1994

[54] GUARDED SCALPEL FOR SURGICAL USE

[75] Inventors: Michael R. Abidin; Steven P. Lehmbeck, both of Baltimore, Md.

[73] Assignee: Leonard Bloom, Towson, Md.; a part interest

[21] Appl. No.: 40,165

[22] Filed: Mar. 30, 1993

Related U.S. Application Data

[63] Continuation-in-part of Ser. No. 825,556, Jan. 24, 1992, Pat. No. 5,250,063.

[51] Int. Cl.5 .................................... A61B 17/32
[52] U.S. Cl. ........................... 606/167; 30/151; 30/335
[58] Field of Search .............. 606/166, 167, 172, 181, 606/182, 185; 30/162, 151, 164, 67, 286, 335; 128/751

[56] References Cited

U.S. PATENT DOCUMENTS

| | | | |
|---|---|---|---|
| 1,914,153 | 6/1933 | Ogden | 30/339 |
| 2,885,780 | 5/1959 | Campbell | 30/162 |
| 3,906,626 | 9/1975 | Riuli | 30/162 |
| 4,491,132 | 1/1985 | Aikins | 606/167 |
| 5,071,426 | 12/1991 | Dolgin et al | 606/167 |

FOREIGN PATENT DOCUMENTS 3722899 1/1989 Fed. Rep. of Germany ...... 606/167

Primary Examiner—Stephen C. Pellegrino
Assistant Examiner—William W. Lewis
Attorney, Agent, or Firm—Leonard Bloom

[57] ABSTRACT

A surgical scalpel (10) is provided with a retractable guard (11) for its cutting blade (12). The guard (11) is mounted on the handle (24) of the scalpel (10) for sliding movement between an advanced position in which the blade (12) is covered and a retracted position in which the blade (12) is exposed. The guard (11) may be moved with one hand, and the surgeon, nurse and/or assistant does not have to take his or her eyes away from the patient or the instrumentation during a surgical procedure. A two-position resiliently-biased manually-releasable detent member (29), is disposed within the longitudinal center plane (30) of the handle (24) and extends above the handle (24). A cut-out (49) on the bottom wall (15) of the guard (11), together with the detent member (29), facilitates the one-hand actuation of the guard (11). A slot (25) on the guard (11) and a pin (26) or the handle (24), limits the sliding movement of the guard (11) independently of the detent action. Two embodiments are disclosed.

3 Claims, 12 Drawing Sheets

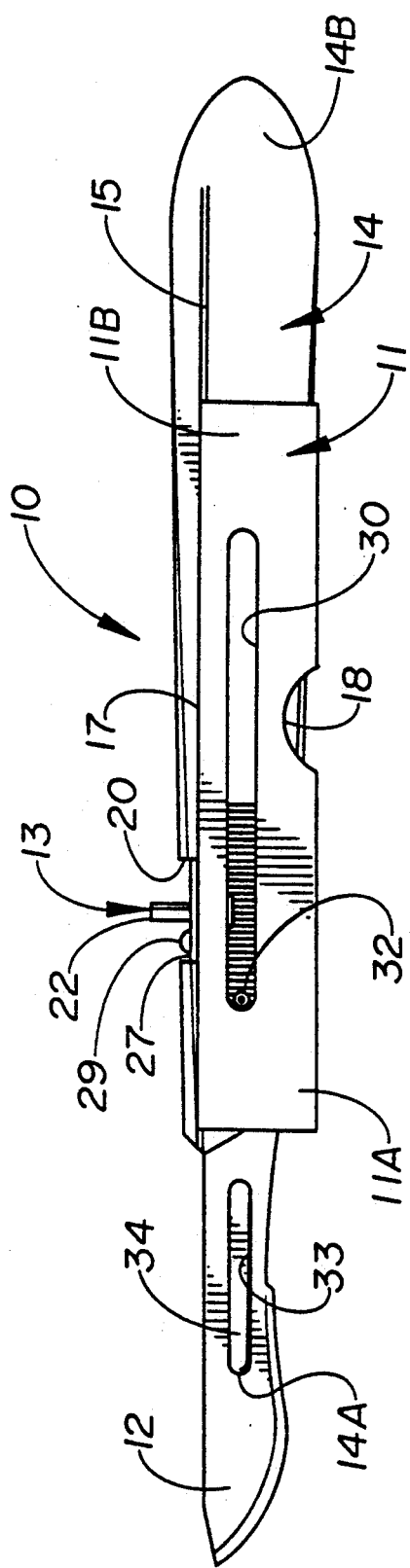
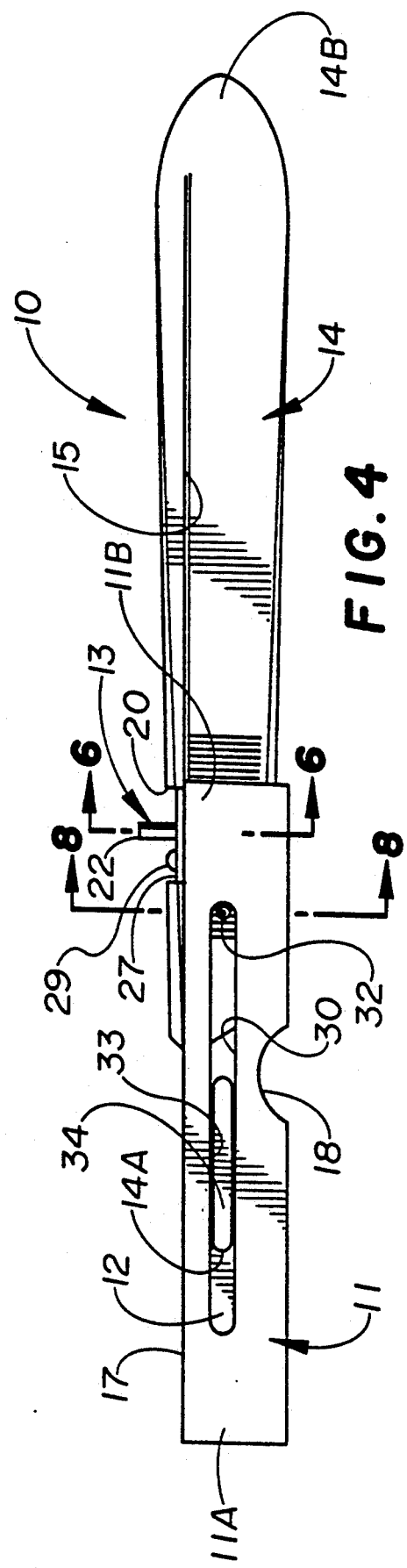

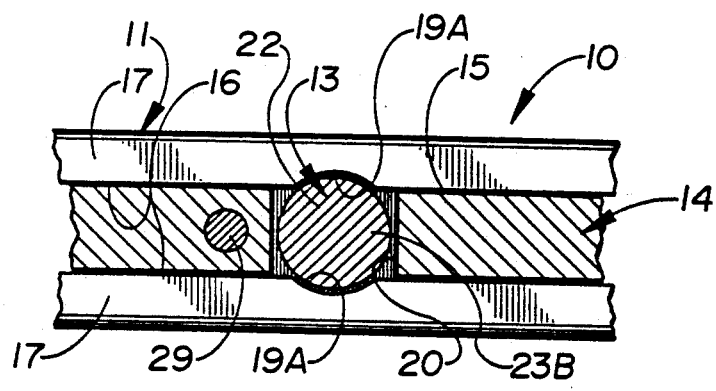
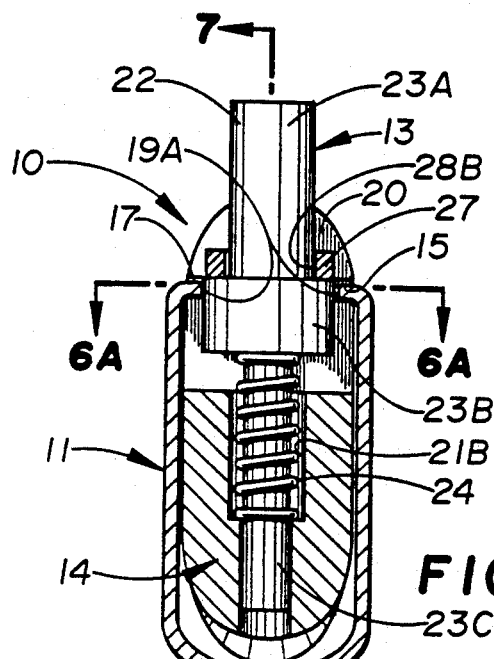
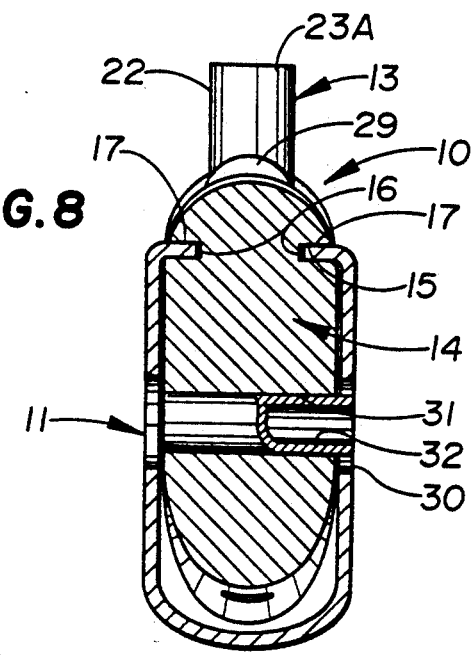
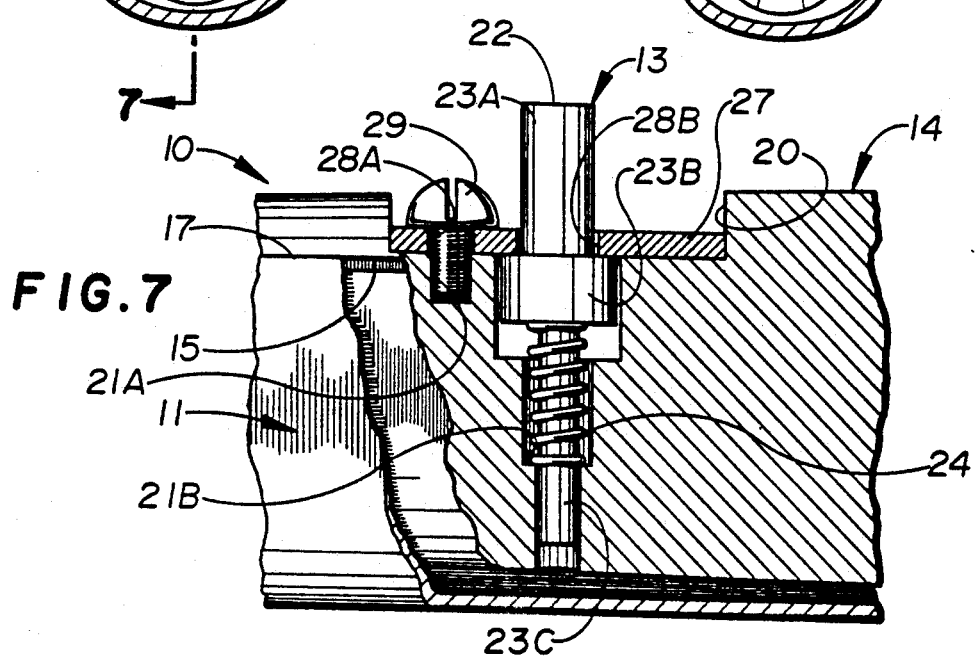

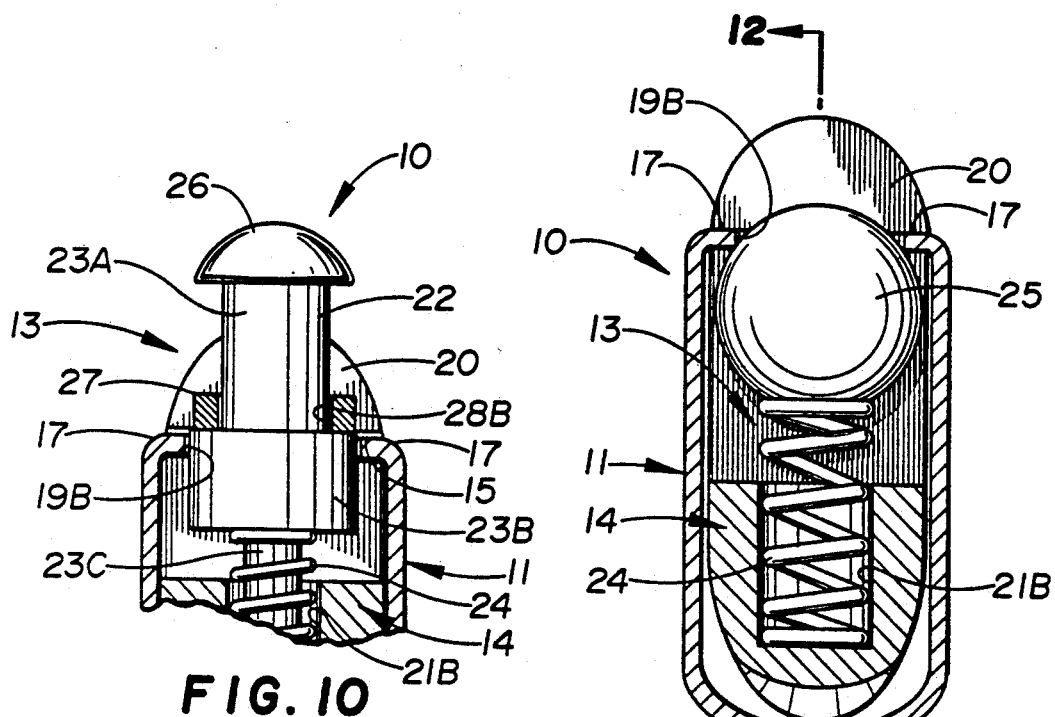
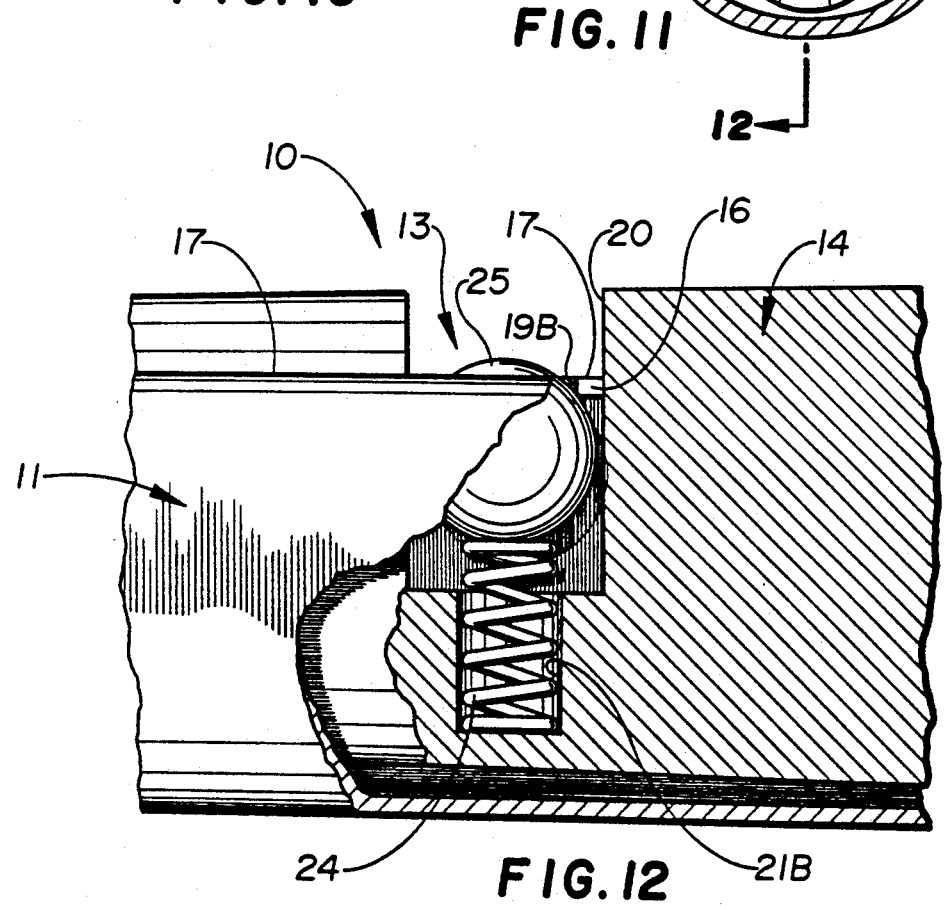

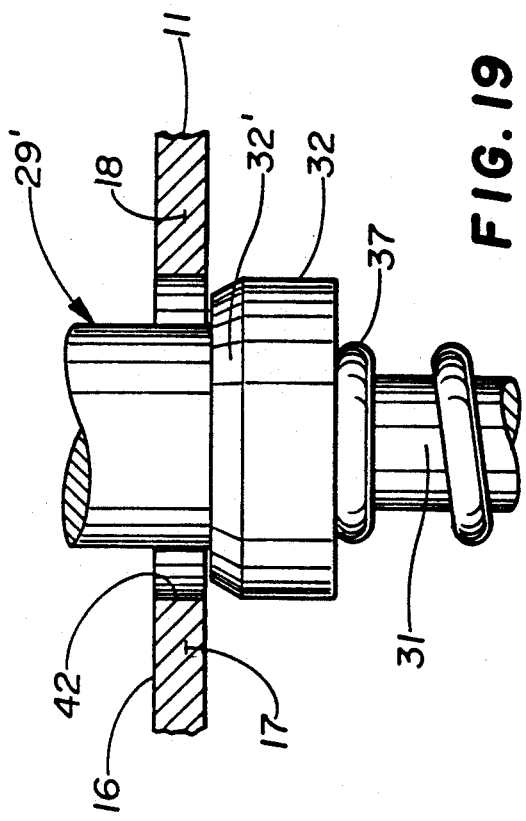
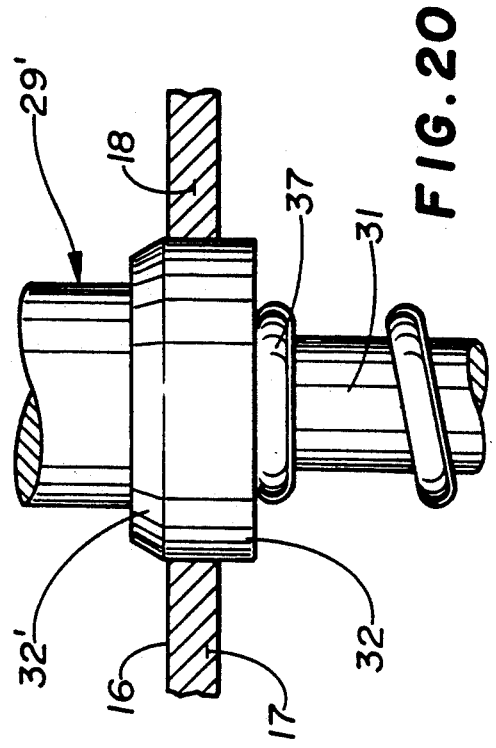
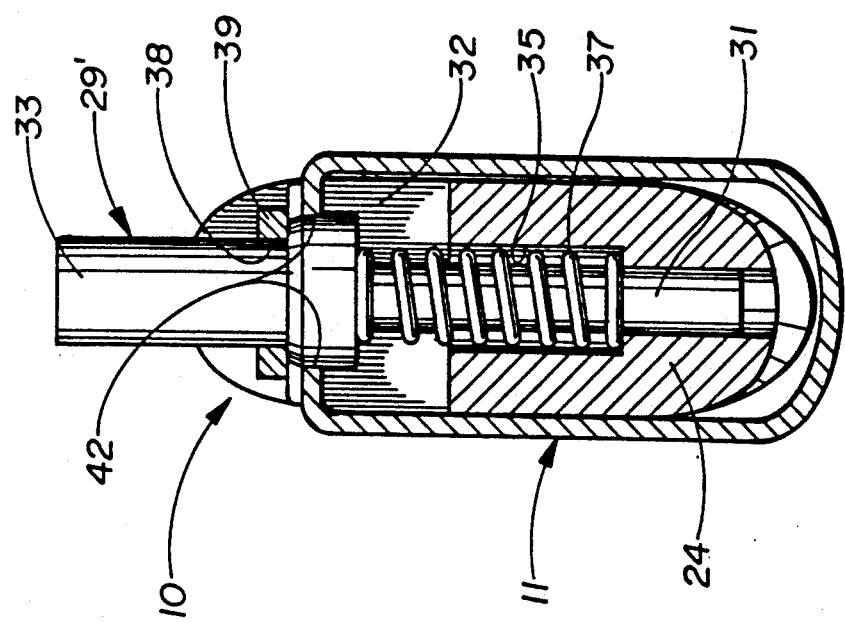

GUARDED SCALPEL FOR SURGICAL USE

CROSS-REFERENCE TO RELATED APPLICATION

The present invention is a continuation-in-part of application Ser. No. 825,556 filed Jan. 24, 1992, now U.S. Pat. No. 5,250,063 for "Surgical Scalpel with Retractable Guard", the disclosure of which is incorporated herein in its entirety.

FIELD OF THE INVENTION

The present invention relates to a surgical scalpel and, in particular, to a surgical scalpel having a retractable blade guard to protect against inadvertent nicks or cuts during a surgical procedure in an operating room.

BACKGROUND OF THE INVENTION

Scalpels are regularly used by surgeons and other health care professionals for making incisions during an operating procedure. Typically, the operating room assistant (which may be a nurse, technician or another doctor) "slaps" the scalpel into the surgeon's hand in a predetermined orientation, so that the surgeon can "feel" the scalpel and automatically grip its handle without taking his or her eyes away from the patient or the instrumentation. If the predetermined orientation is not closely followed, the nurse's or surgeon's hand may be cut or nicked. The same hazard may be encountered when the surgeon transfers the scalpel back to the assistant.

These nicks or cuts, besides being uncomfortable and distracting, may result in blood or body fluid exposure from the patient to the surgeon or other health care professional (and vice versa) and hence may lead to the spreading of infectious diseases. Concern over this situation has become especially acute since the appearance of the human immune deficiency virus (or "HIV"). Indeed, such cuts have already been blamed, by some health care providers, for cases of HIV infection in their profession. consequently, some individual surgeons or health care providers have stopped performing surgical operations, rather than risk the chances of inadvertently contracting the deadly HIV from an infected patient. There are similar concerns with the Hepatitis B virus (or "HBV").

The risks associated with scalpel cuts during an operating room procedure are greater than those associated with needle sticks; but even there, the problem is becoming alarming. In a study made by the Needle Stick Surveillance Group of the Centers For Disease Control ("CDC") out of 3,978 known punctures from patients known to be HIV positive, 13 health care workers got infected or roughly 1 out of 300. Thus, from a single needle stick while treating an AIDS patient in an operating room or other environment, the chances are roughly 1 out of 300 that the surgeon, nurse or other individual health care provider will sero-convert and become HIV positive. If a surgeon, nurse or assistant is cut by a scalpel while conducting a surgical procedure in an operating room (rather than a needle stick) the risk is much greater simply because, first, there is more blood involved and, secondly, the surface area of the wound is larger.

In order to solve this problem, the prior art has disclosed guarded scalpels. Examples are U.S. Pat. Nos. 3,906,626 and 5,071,426 and German Offenlegungsschrift DE 37 22 899 A1. However, and for various reasons, these guarded scalpels are not completely satisfactory; hence are not in current widespread use in hospitals and clinics.

The prior art has also disclosed a microsurgical knife with a locking blade guard, as for example, U.S. Pat. No. 4,735,202 used for ophthalmological purposes. The structure and intended purpose, however, are not suitable for general surgical use.

Another example of the prior art is U.S. Pat. 4,499,898, which discloses a surgical knife with a controllably extendable blade and a gauge therefor. Again, this disclosure is intended for very delicate surgery and is not suitable for a general purpose guarded scalpel.

While protective gloves aid in reducing the chances of being cut during a surgical procedure, these gloves are by no means foolproof; and such cuts are still quite common. Even when two sets of gloves are utilized, full protection is not afforded to the health care provider, for many times the blade cuts right through both sets of gloves. Also, utilizing two sets of gloves reduces finger dexterity and is distracting, interfering with the intended surgical procedure.

This situation has become so pronounced that some leading surgeons, as well as nurses and other individual health care providers, have abandoned their respective practices altogether.

In the operating room, time is of the essence and seconds count; the mental concentration and physical effort are intense; and distractions must be avoided at all times.

SUMMARY OF THE INVENTION

Accordingly, the present invention provides a guarded scalpel for general surgery, wherein the blade guard may be retracted and advanced, alternately, and in a one-hand operation without taking one's eye away from the patient or the instrumentation. When transferring the guarded scalpel from the nurse to the surgeon and vice versa, the recipient will know intuitively from the "feel" of the guarded scalpel itself that, first, the guard has been advanced to cover the blade and, second, the relative orientation of the guarded scalpel itself, that it, whether the cutting edge on the covered blade is "up or "down".

The guard closely follows the slim-line contours of the scalpel handle, so that the guard is not cumbersome or obtrusive; rather, the guarded scalpel has a good "feel" and balance, is comfortable to use, and does not distract the surgeon nor interface with his or her concentration.

Moreover, a two-position resiliently-biased detent means provides an auditory "click", signalling that the guard has been moved into an alternate position, and precluding an inadvertent and undesirable movement of the guard during transfer or use of the guarded scalpel. This detent means may be manually released—in a one-hand movement without taking one's eyes off the patient or the instrumentation—for movement of the guard into an alternate position.

The detent means includes a resiliently-biased detent member carried by the handle, disposed substantially within the vertical longitudinal center plane thereof, and projecting above the handle for convenient manual manipulation. The detent member has a limited movement with respect to the handle about an axis which is substantially perpendicular to the longitudinal axis of the guard, thereby minimizing the external contours of the guarded scalpel.

The detent member cooperates with a pair of longitudinally-spaced detent pockets; and, preferably, the detent member has a self-aligning tapered portion, thereby providing a solid detent action between the handle and the guard, and thereby accommodating tolerance accumulations in the manufacture and assembly of the guarded scalpel.

A stop means is provided between the guard and the handle, and this stop means is independent of the detent means.

In a preferred embodiment, the guard further has a bottom wall provided with a cut-out, such that the relative orientation of the guarded scalpel is readily appreciated by the recipient without taking his or her eyes away from the patient, and such that the projecting portion of the detent member may be depressed to release the detent means while the cut-out on the bottom wall of the guard may be engaged to retract or advance the guard—all in a one-handed operation.

The present invention thus substantially reduces the risk of the surgeon, nurse or assistant inadvertently acquiring (or transmitting) an infectious disease, such as HIV or HBV, in the operating room or similar medical environment.

These and other objects of the present invention will become readily apparent from a reading of the following description of the present invention, taken in conjunction with the enclosed drawings.

BRIEF DESCRIPTION OF THE DRAWINGS

FIG. 4 is a side elevation of the scalpel of the present invention with the protective guard in a first advanced position to cover the blade.

FIG. 5 is a side elevation of the scalpel of the present invention with the protective guard in a second retracted position, thereby exposing the blade.

FIG. 6 is a cross-sectional view, taken along lines 6—6 of FIG. 4, drawn to an enlarged scale, and showing the manually-releasable detent means for the guard.

FIG. 6A is a cross-sectional view thereof, taken across the lines 6A—6A of FIG. 6, and showing the annular collar on the spring-loaded detent pin received in a respective detent pocket formed on the guard.

FIG. 7 is a cross-sectional view taken along lines 7—7 of FIG. 6, showing the means for retaining the detent means on the body or handle of the scalpel.

FIG. 8 is a cross-sectional view taken along lines 8—8 of FIG. 4, drawn to an enlarged scale, and showing the stop means for the guard.

FIG. 10 corresponds substantially to FIG. 6, but shows a cap or button on the releasable detent means for the blade, thereby providing a preferred tactile means and facilitating manual release of the detent means.

FIG. 11 is an alternate embodiment of the detent means.

FIG. 12 is a cross-sectional view thereof, taken along lines 12—12 of FIG. 11.

FIG. 18 corresponds substantially to FIG. 6, but shows a tapered portion of the detent member received within a respective detent pocket, thereby providing an improved detent action between the guard and the handle of the guarded scalpel.

FIG. 19 is an exploded elevational view, corresponding substantially to a portion of FIG. 18 drawn to an enlarged scale, and showing the tapered portion of the detent member initially engaging a respective detent pocket.

FIG. 20 shows the detent member fully seated in its respective detent pocket.

GENERAL DESCRIPTION OF THE PREFERRED EMBODIMENTS

Figure 1:
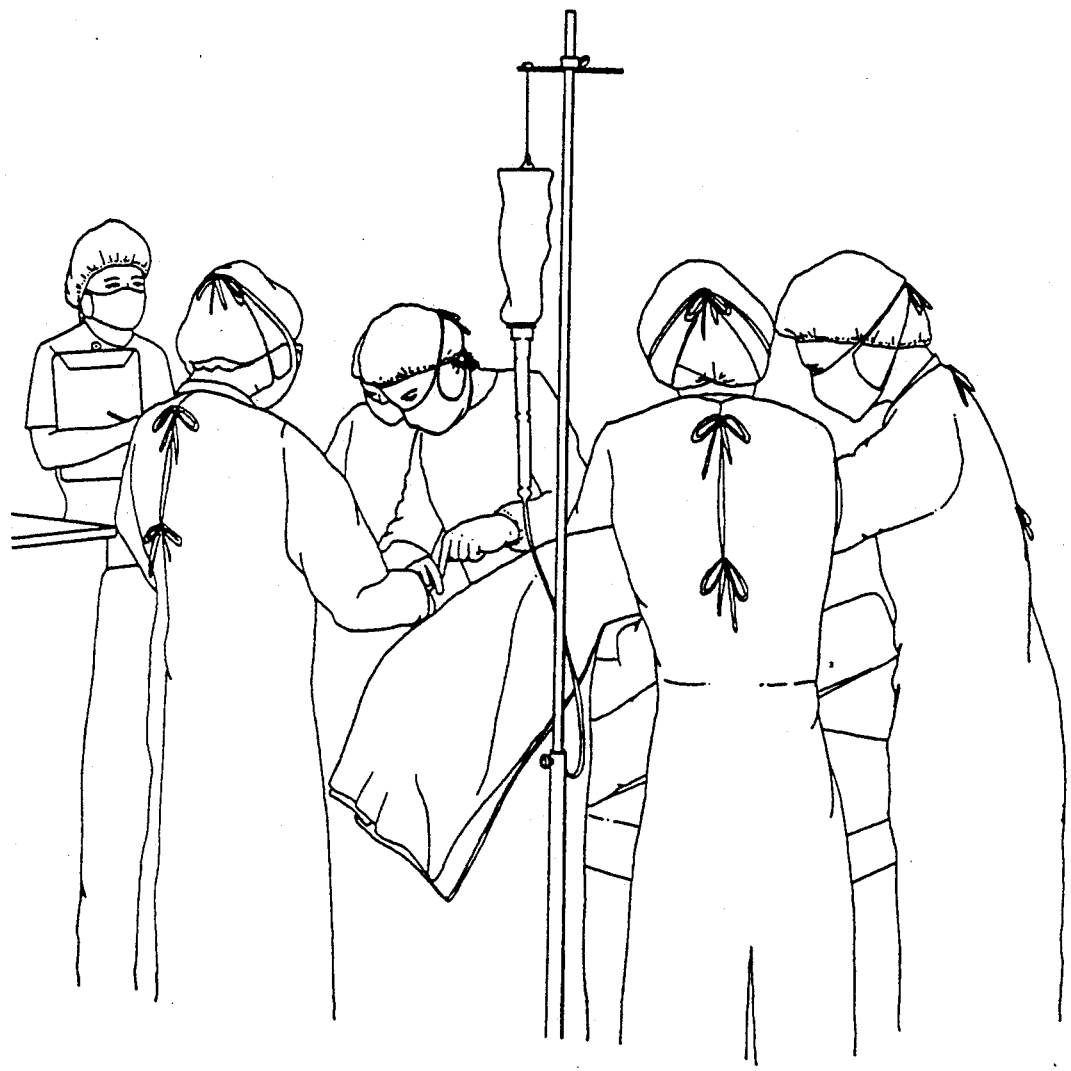
FIG. 1 is a perspective view of an operating room or theater where the improved surgical scalpel, equipped with the protective blade guard of the present invention, will be utilized.
Figure 2A:
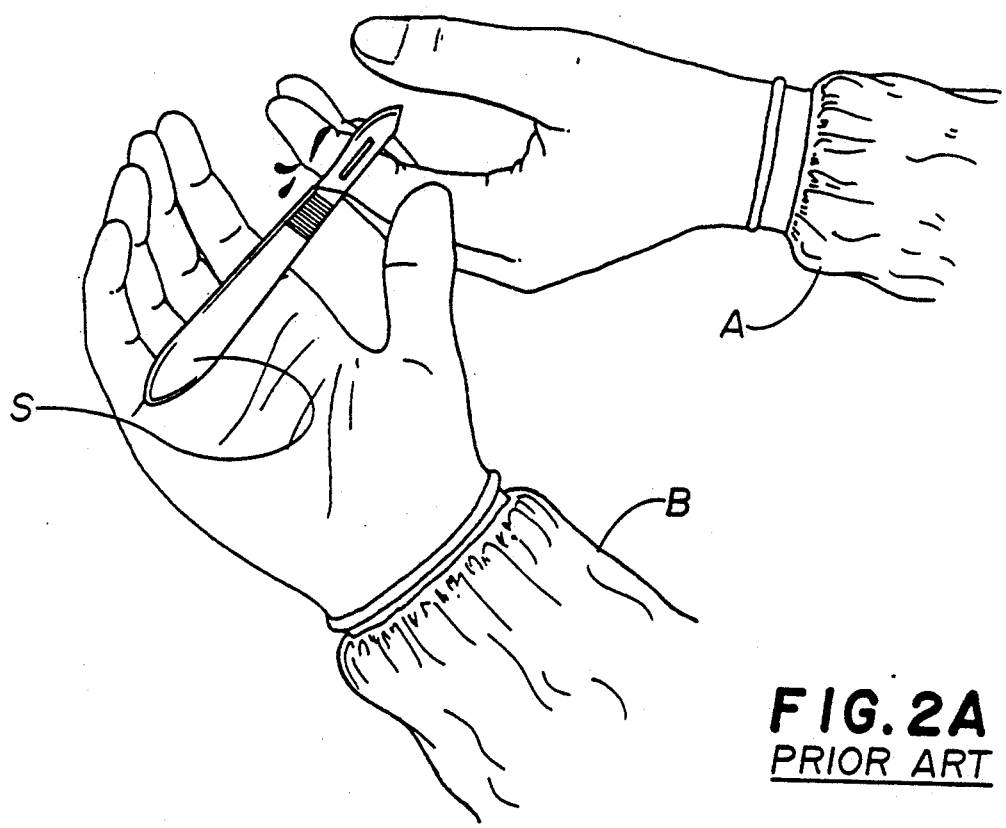
FIG. 2A is an enlarged view of a conventional (unguarded) scalpel, illustrating how an assistant may be cut or nicked when transferring the scalpel during an operating procedure.
Figure 2B:
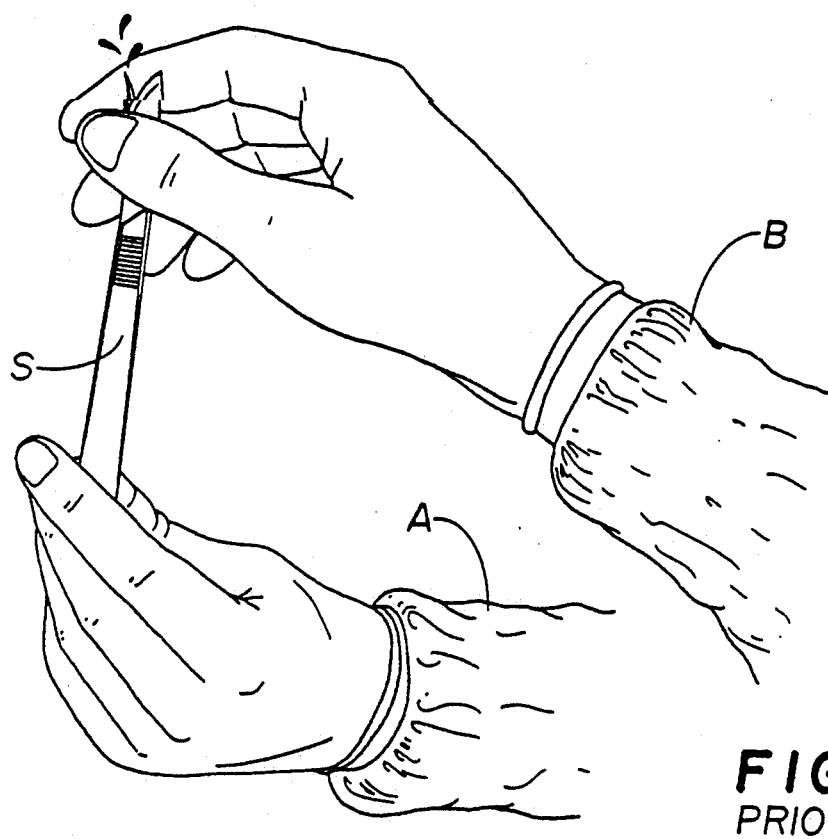
FIG. 2B is an enlarged view of a conventional scalpel, corresponding substantially to FIG. 2A, but showing how the surgeon may be cut or nicked when transferring the scalpel.

With reference to FIGS. 1, 2A and 2B, the situation in a typical operating room ("O.R.") is tense and, quite often, the patient's life is at stake. The scalpel blade is very sharp; and in passing a conventional unguarded scalpel S from the nurse (or other assistant) A to the surgeon B, and vice versa, it is not at all unusual for the surgeon B or the nurse A to be nicked or cut by the scalpel blade, as shown in FIGS. 2A and 2B. This is a dangerous situation, especially aggravated by current viruses and, besides, is painful and distracting.

Figure 3A:
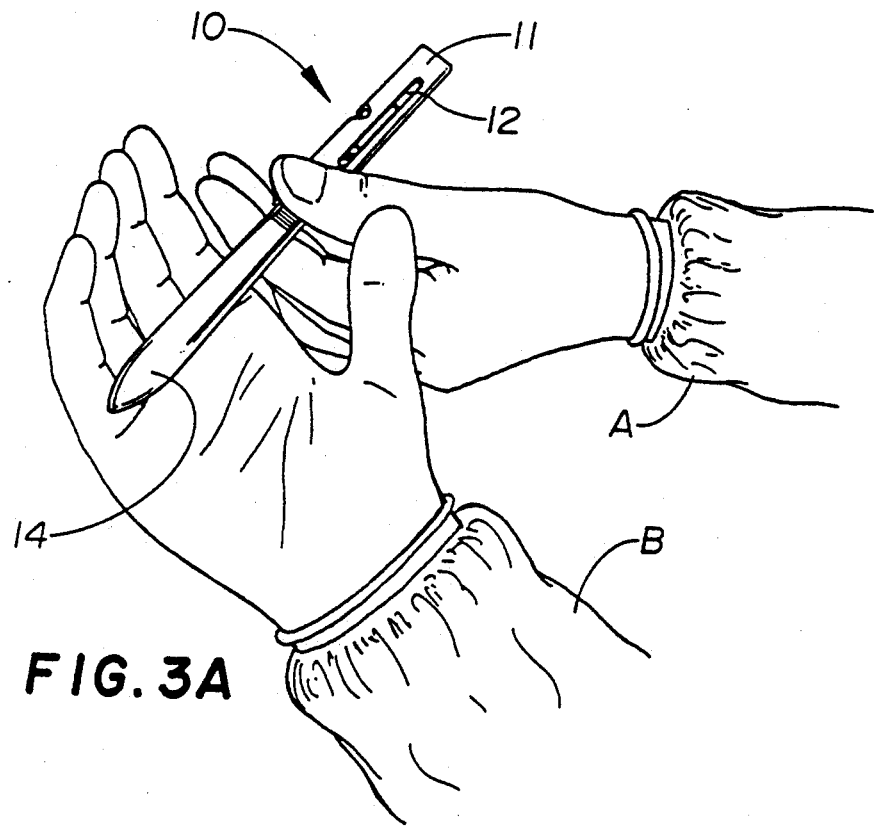
FIG. 3A illustrates how the improved scalpel of the present invention protects the assistant's hand when passing the scalpel to the surgeon during an operation.
Figure 3B:
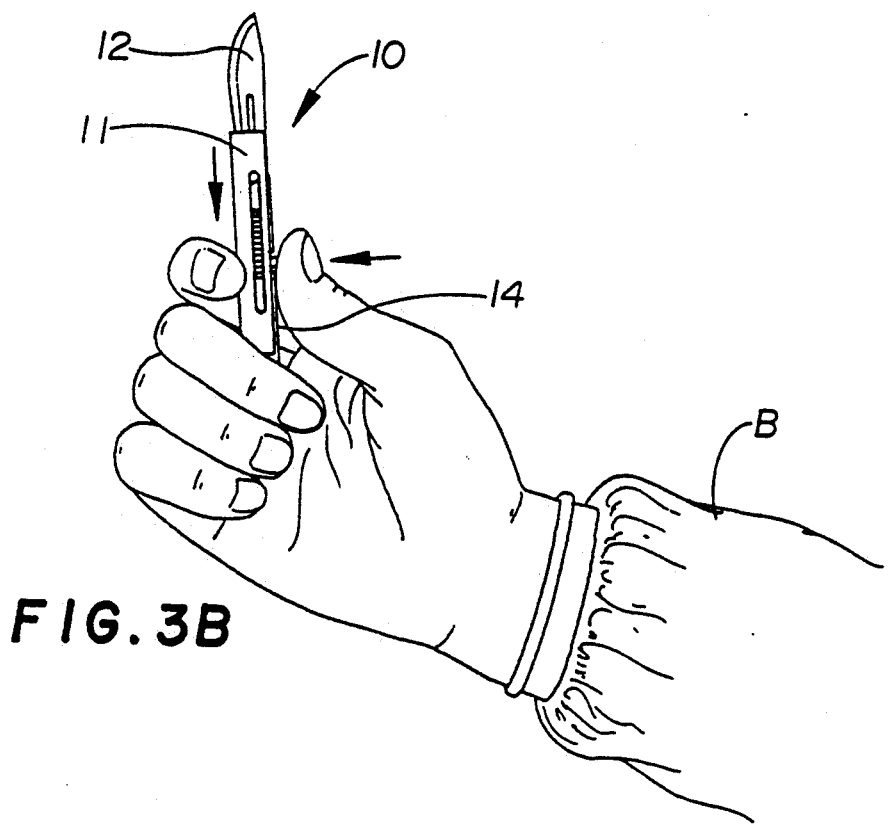
FIG. 3B illustrates how the guard on the improved scalpel is easily and conveniently retracted by the surgeon—with one hand—to expose the blade.
Figure 3C:
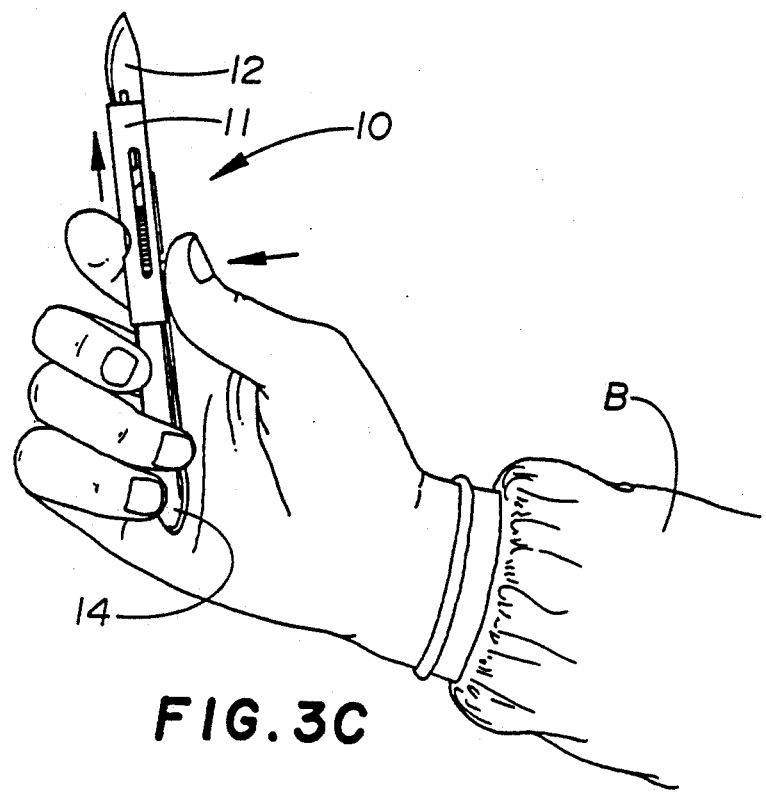
FIG. 3C illustrates how the guard is easily and conveniently advanced by the surgeon—again, with only one hand—to cover the blade.
Figure 3D:
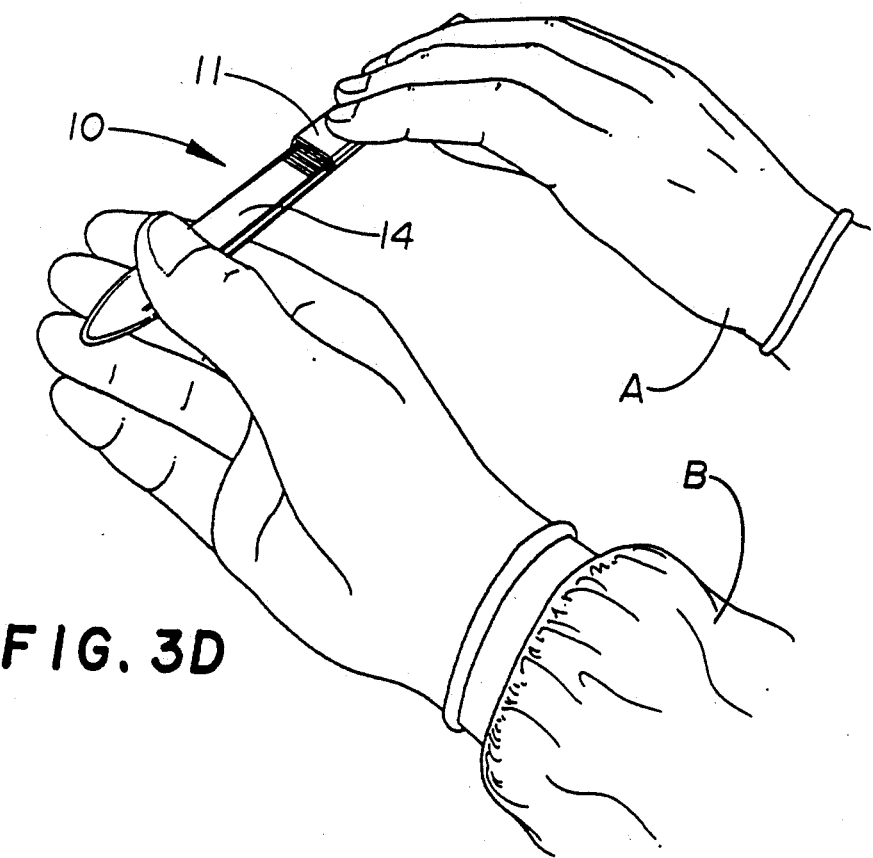
FIG. 3D illustrates how the guarded scalpel of the present invention protects the assistant's hand when the surgeon passes the scalpel back to the assistant.
Figure 9:
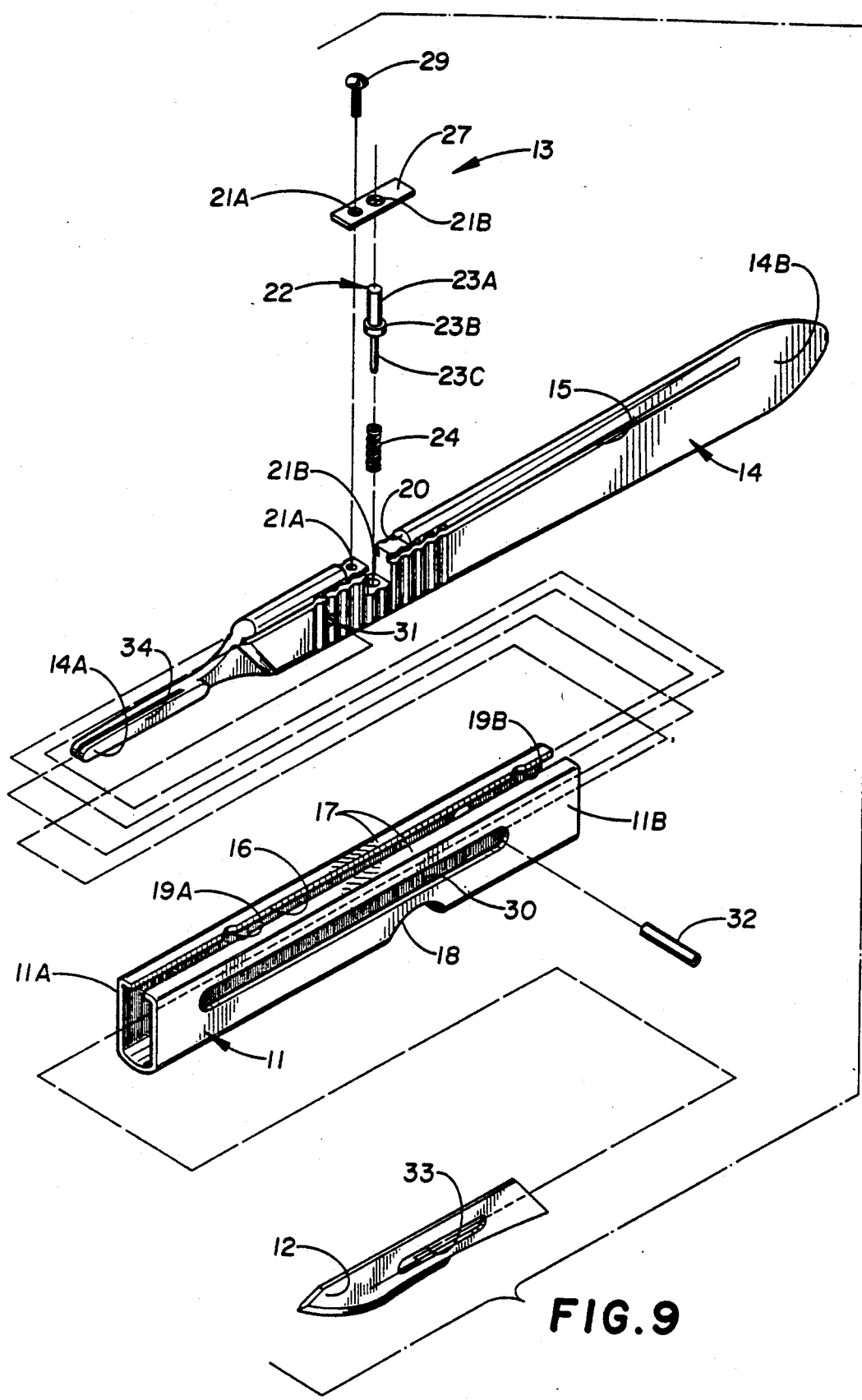
FIG. 9 is an exploded perspective view of the improved scalpel with its blade guard.

Accordingly, and with reference to FIGS. 3A-D, the guarded scalpel 10 of the present invention has a unique guard 11 for the blade 12. The blade 12 is conventional and is removably mounted on the scalpel 10 (as hereinafter described). The scalpel 10 may be passed from the nurse A to the surgeon B in an guarded position (FIG. 3A) to prevent the nurse from being cut. Thereafter, the surgeon may retract the guard 11 in a one-handed movement (FIG. 3B) to expose the blade 12. After making one or more incisions, the surgeon may advance the guard (FIG. 3C)—again, in a one-handed movement and without taking his or her eyes away from the patient or the instrumentation in the O.R.—and pass the scalpel 10 back to the nurse (FIG. 3D). The risk of getting cut has been substantially reduced, if not eliminated altogether.

It will be appreciated, of course, that various guarded scalpels 10 may be passed back and forth in the O.R. during a lengthy procedure on a patient.

With reference to FIGS. 4-9, the guard 11 is substantially Unshaped and closely conforms to the outer contours of the scalpel 10. The guard 11 includes parallel side walls 13 and 14, a bottom wall 15, and a top portion 16. The top portion 16 includes a pair of inturned flanges 17 and 18, respectively, defining a slot 19 therebetween. These inturned flanges 17 and 18 are received in longitudinal guide tracks 20 and 21 formed in the sides 22 and 23, respectively, in the body portion or handle 24 of the scalpel 10, thereby slidably mounting the guard 11 on the handle 24.

A stop means is provided to limit the sliding movement of the guard 11. Preferably, the side wall 14 of the guard 11 has a closed longitudinal slot 25 formed therein; and a pin 26 passes through the closed longitudinal slot 25 and is secured within a transverse bore 27 in the handle 24, thereby restricting the longitudinal sliding movement of the guard 11 and defining its alternate advanced and retracted positions, respectively. Preferably, the pin 26 is a split sleeve as shown more clearly in FIG. 8.

A two-position resiliently-biased manually-manipulatable detent means 28 is provided between the guard 11 and the handle 24 of the scalpel 10. This detent means 28, which is manually releasable, positively locks the guard 11 in its selected position and precludes inadvertent or accidental movement thereof.

The preferred detent means 28 includes a resilient-biased detent member 29. The detent member 29 is carried by the handle 24 and is disposed substantially within the (vertical) longitudinal midplane or center plane 30 thereof, as shown more clearly in FIG. 6, and about an axis which is substantially perpendicular to the longitudinal axis of the guard 11. Thus, the detent member 29 is backed up substantially by the material portion of the handle 24—the detent member 29 is not disposed laterally thereof—and minimizes the extended outer contours of the guarded scalpel 10.

The detent member 29 includes a stem 31, an intermediate collar 32, and an upwardly-projecting portion or button 33. The handle 24 has a bore 34 communicating with a counterbore 35 and a cross-cut 36, respectively. Stem 31 of the detent member 29 is slidably guided in the bore 34, so that the detent member 29 has a smooth inward movement without being cocked. A coil spring 37 is within the counterbore 35 and bears against the collar 32, thereby constantly urging the detent member 29 outwardly (upwardly) of the handle 24; and the collar 32 is slidably received within the cross-cut 36. The button 33 passes through an opening 38 in a retaining plate 39, and the retaining plate 39 is secured to the handle 24 by a screw 40 received in a tapped recess 41. As shown more clearly in FIGS. 6A and 9, a pair of longitudinally-spaced detent pockets 42 and 43 are formed in the inturned flanges 17 and 18 on the guard 11 to receive, alternately, the collar 32 on the detent member 29.

When the detent member 29 is manually depressed inwardly against the force of the coil spring 37, the collar 32 clears its respective detent pocket 42 or 43 and allows the guard 11 to be slidably moved along the handle 24 and into its alternate position. When the collar 32 is received in detent pocket 42, the guard is advanced (forwardly) on the handle 24 to cover the blade 12 and prevent accidental contact with the blade 12 during transfer of the scalpel 10; and when the collar 32 is received in detent pocket 43, the guard 11 is retracted (rearwardly) on the handle 24 to expose the blade 12 during an operating procedure.

To facilitate depression of the detent member 29, a cap 44 may be provided (as shown more clearly in FIG. 10).

With reference to FIGS. 11 and 12, an alternate embodiment of the detent member 29 comprises a detent ball 45 resiliently biased by a spring 46. The spring 46 is in a blind bore 47, and the detent ball 45 is slidably guided in a counterbore 48.

With reference again to FIGS. 4, 5 and 9, the bottom wall 15 of the guard 11 has a cut-out 49 extending upwardly into the respective side walls 13 and 14 of the guard 11. This cut-out 49 is intended to receive either the thumb or forefinger of the recipient and thereby facilitate manual movement of the guard 11.

With reference to FIGS. 13A-D and 14A-D, the features and advantages of the present invention will be readily appreciated.

When the guarded scalpel 10 is placed in the hand of the surgeon (or passed back to the nurse), the surgeon (or nurse) will know intuitively from the "feel" of the scalpel 10, first, that the guard 11 is "on" (that is, the blade 12 is covered by the guard 11) but will also know, secondly, the orientation of the scalpel 10 (that is, whether the cutting edge of the blade 12 is pointed "up" or "down"). Most surgeons prefer to make incisions with the blade 12 "down", some with the blade 12 "up", and some surgeons use both orientations depending upon the nature of the required incision.

Figure 13A:
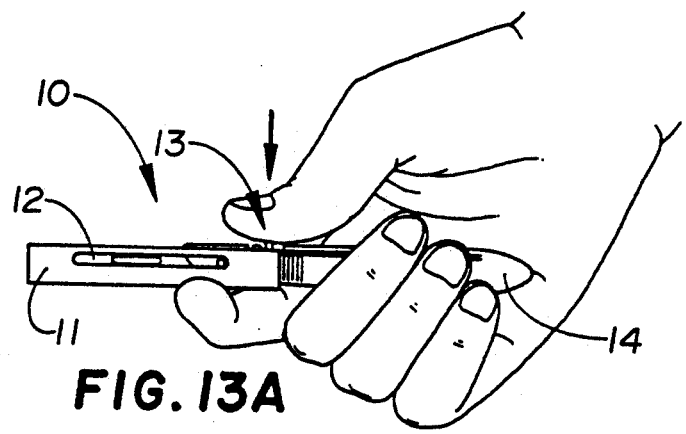
FIGS. 13A–13D show, respectively, the manner in which the guard may be manually retracted to expose the blade on the scalpel, and then advanced to cover the blade to protect against inadvertent cuts and nicks normally occasioned in transferring the scalpel from the nurse to the surgeon, and vice versa, during a surgical procedure; wherein the thumb engages the releasable detent pin (or button) and the forefinger is received in the cut-out formed in the bottom wall of the Unshaped sliding guard to alternately retract and advance the guard.
Figure 13B:
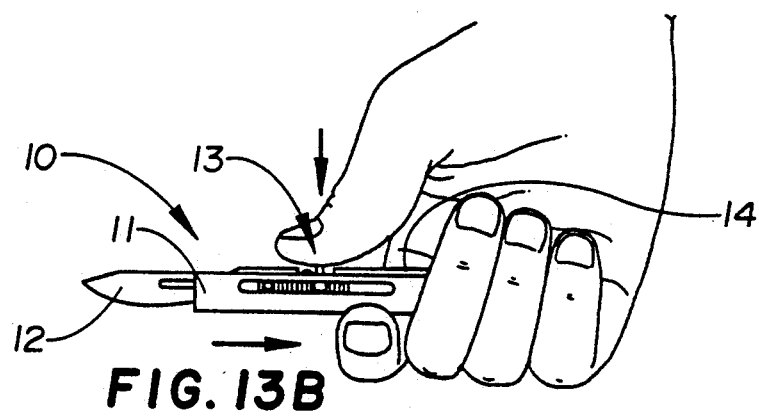
Figure 13C:
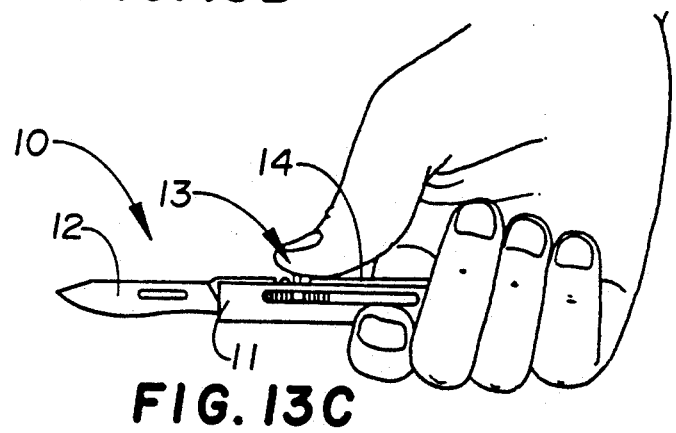
Figure 13D:
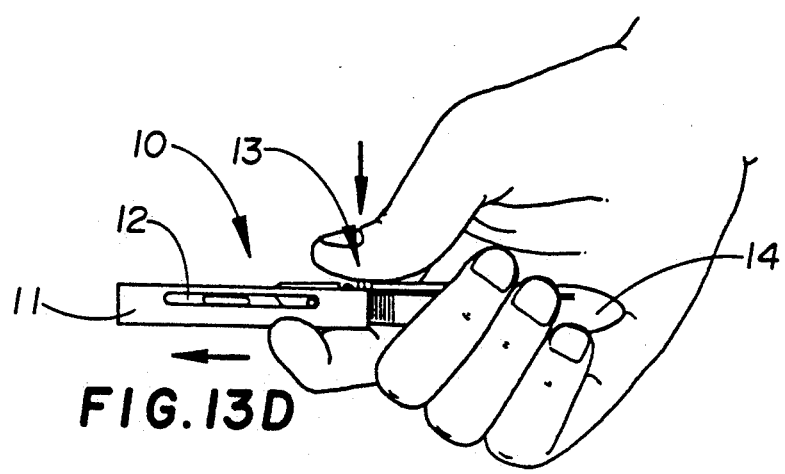
Figure 14A:
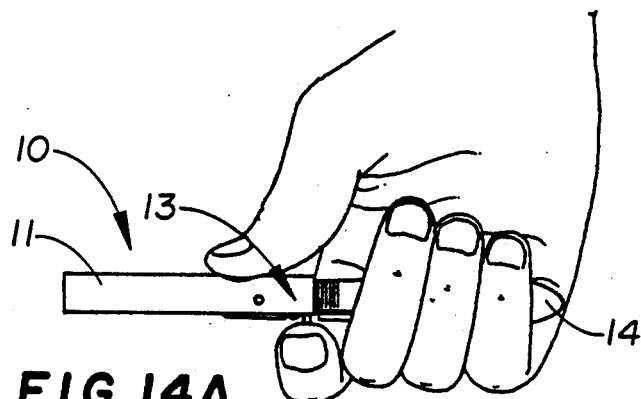
FIGS. 14A–14D correspond substantially to that of FIGS. 13A–13D, but show an alternate manner for selectively and alternately retracting and advancing the sliding guard, wherein the forefinger releases the detent pin, and wherein the thumb engages the cut-out in the bottom wall of the guard; the surgeon may then use the scalpel to cut in a generally upwardly direction or may pivot his or her wrist to cut in a generally downwardly direction, as desired.
Figure 14B:
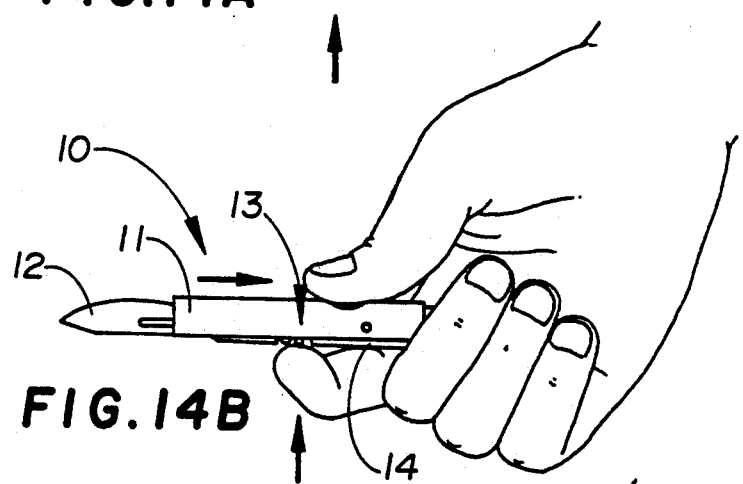
Figure 14C:
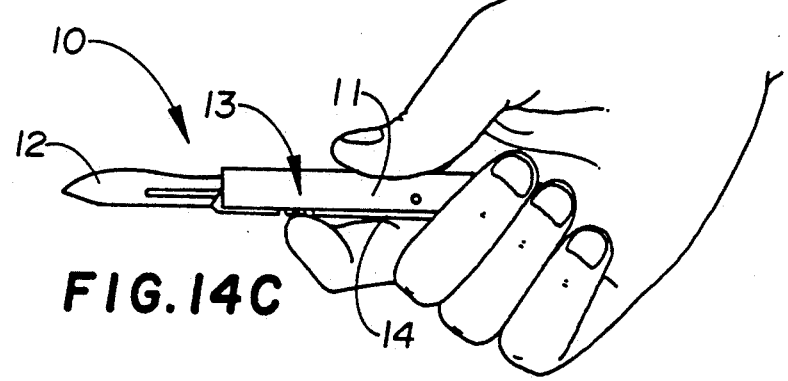
Figure 14D:
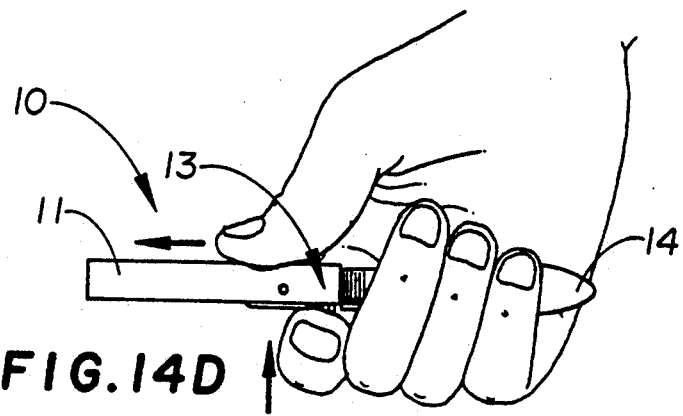

In FIGS. 13A-D, the blade 12 is "down". In FIG. 13A, the surgeon grasps the scalpel 10, such that the surgeon's thumb is on the upwardly-projecting button 33 on the detent member 29, and the surgeon's forefinger is in the cut-out 49. In FIG. 13B, the button 33 is depressed, and the guard 11 is moved rearwardly to expose the blade 12. After the incision (or incisions) have been made, the button 33 is again depressed by the surgeon's thumb while the surgeon's forefinger is in the cut-out 49 (FIG. 13C) and, thereafter, the guard 11 is moved forwardly (FIG. 13D) to cover the blade 11.

In FIGS. 14A-D, a similar sequence is followed. There, however, the cutting edge of the blade is "up", and the surgeon's thumb is in the cut-out 49 while his or her forefinger is on the button 33.

In summary, the features and advantages of the present invention are as follows: When the scalpel 10 is passed from the nurse to the surgeon (for example) the surgeon knows intuitively from the "feel" of the scalpel 10 that the guard 11 is "on", covering the blade 12, and that the edge on the blade 12 is either "up" or "down". The surgeon may retract the guard 11, easily and conveniently, using only one hand and without taking his (or her) eyes away from the patient or the instrumentation in the operating room. The detent means is within the "meaty" portion of the handle 24, that is, within the (vertical) longitudinal center plane 30 thereof, thereby taking maximum advantage of the handle material and, conversely, facilitating a strong detent action. This strong detent action between the guard 11 and the handle 24 provides not only a tactile indication, but also an auditory "click" that the guard 11 has been moved into its alternate desired position, that is, retracted to expose the blade 12 or advanced to cover the blade 12. The detented action is "solid" and prevents inadvertent or accidental movement of the guard 11 during a surgical procedure or in transferring the scalpel 10. A stop means between the guard 11 and the handle 24, including the closed slot 25 and the transverse pin 26, is independent of the detent means itself; this improves the reliability of the instrument. The guard 11 closely straddles the handle 24 and maintains the desired "slim line" appearance; and the added weight of the guard 11 is relatively insignificant and does not detract from the overall balance, feel and handling of the lightweight scalpel 10. The components of the overall assembly of the scalpel 10 may be manufactured conveniently and economically out of readily available materials, and the scalpel may be sterilized in an autoclave for repeated usage.

Figure 15:
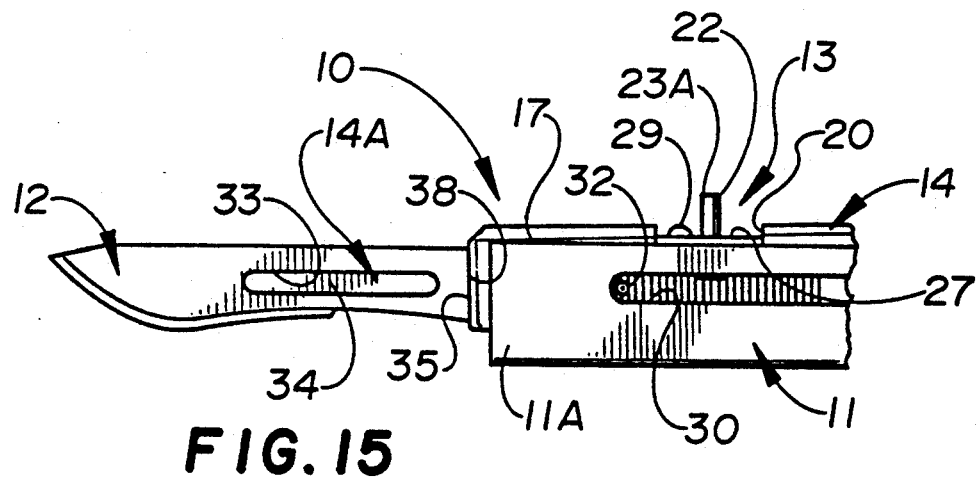
FIG. 15 is a side elevational view of an improved blade mounted on the scalpel.
Figure 16:
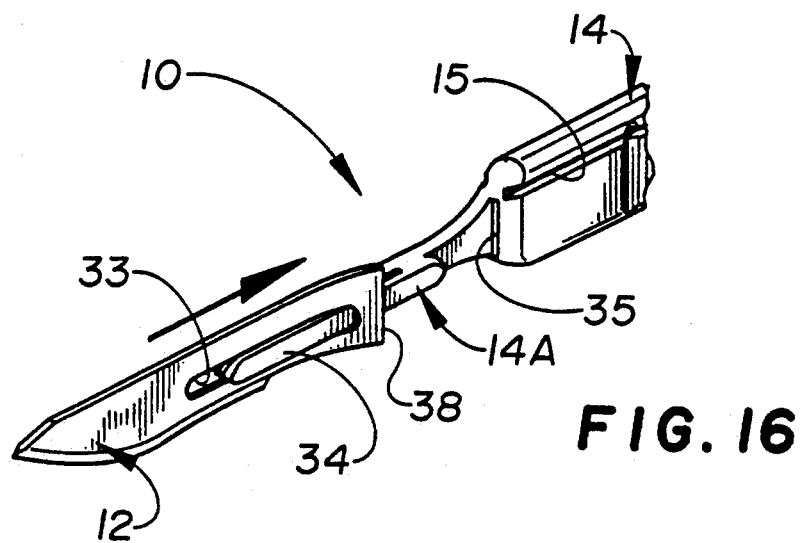
FIG. 16 is a partial exploded view, corresponding substantially to FIG. 15, but showing the manner in which the improved blade is mounted on the scalpel.
Figure 17:
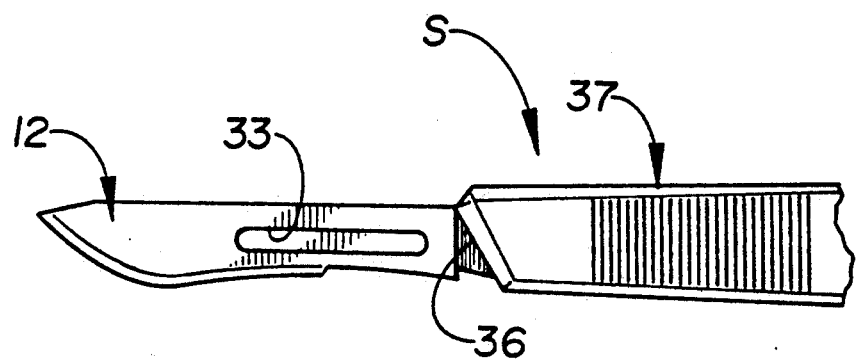
FIG. 17 is a side elevational view of the improved blade of the present invention mounted on a conventional (non-guarded) surgical scalpel.

With reference to FIGS. 15-17, the blade 12 has a closed slot 50 which fits over a laterally-extending longitudinal rib 51 formed on the forward end 52 of the handle 24, thereby removably mounting the blade 12 to the scalpel 10.

In a preferred embodiment, as shown more clearly in FIGS. 15 and 16, the forward end 52 of the scalpel body 10 has a shoulder 53 substantially at right angles thereto. This shoulder 53 corresponds to an angled shoulder 54 on a conventional non-guarded scalpel S as shown in FIG. 17. The angled shoulder 54 cooperates with a conventional blade (not shown) having a rearward angled portion complementary to the angled shoulder 54.

The improved blade 12 of the present invention has a rearward shoulder or edge 55 which is substantially at right angles thereto (as shown more clearly in FIG. 16) and complementary to the right angle shoulder 53 on the scalpel 10. Thus the improved blade 12 fits snugly against the shoulder 53 when the blade 12 is removably mounted on the scalpel 10.

The conventional scalpel blades (not shown) cannot be fitted to the improved scalpel 10 of the present invention. However, and as shown more clearly in FIG. 17, the improved blade 12 of the present invention can be fitted to a conventional non-guarded scalpel S, if desired, as well as to the improved scalpel 10 of the present invention.

With reference to FIGS. 18-20, the detent member 291 has an externally-tapered self-aligning portion 32', thereby piloting the detent member 29' into its respective detent pocket 42 and assuring a "solid" detent action between the guard 11 and the handle 24, and thereby compensating for any misalignments or tolerance accumulations in the manufacture and assembly of the guarded surgical scalpel 10.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. In a guarded scalpel for surgical use, wherein the guarded scalpel includes a handle and further includes a blade mounted forwardly on the handle, and wherein a guard is slidably mounted on the handle for longitudinal movement thereon, the guard having an advanced position in which the blade is covered and a retracted position on which the blade is exposed, the improvement comprising a resiliently-biased manually-releasable detent means between the guard and the handle, thereby providing a positive locking of the guard in its selected position and precluding inadvertent movement thereof, and the detent means including a detent member carried by the handle and cooperating, alternately, with a pair of spaced-apart detent pockets formed in the guard, and the detent member having an externally-tapered self-aligning portion engaging a respective detent pocket, thereby providing a good detent action between the guard and the handle, and thereby accommodating tolerance accumulations in the manufacture and assembly of the guarded scalpel.

2. In a guarded scalpel for surgical use, wherein the guarded scalpel includes a handle and further includes a blade mounted forwardly on the handle, and wherein a guard is slidably mounted on the handle for longitudinal movement thereon, the guard having an advanced position in which the blade is covered and a retracted position on which the blade is exposed, the improvement comprising a resiliently-biased manually-releasable detent means between the guard and the handle, thereby providing a positive locking of the guard in its selected position and precluding inadvertent movement thereof, and stop means between the guard and the handle to limit the sliding movement of the guard, the stop means being independent of the detent means.

3. In a guarded scalpel for surgical use, wherein the guarded scalpel includes a handle and further includes a blade mounted forwardly on the handle, and wherein a guard is slidably mounted on the handle for longitudinal movement thereon, the guard having an advanced position in which the blade is covered and a retracted position on which the blade is exposed, the improvement comprising a two-position detent means between the guard and the handle and including a manually-releasable resiliently-biased detent member projecting beyond the guard, such that the user's thumb may depress the detent member to thereby release the guard from its detented position, and the guard having a manually-engagable portion independent of the detent member and engaged by the user's forefinger to effect a sliding movement of the guard on the handle, subsequent to the release of the detent means, whereby the guard may be moved from one position into another position in a one-hand operation without requiring the user to view the scalpel.

* * * * *